(12) United States Patent
Bokis et al.

(10) Patent No.: US 11,236,028 B2
(45) Date of Patent: Feb. 1, 2022

(54) PRODUCTION AND USE OF 3,4' AND 4,4'-DIMETHYLBIPHENYL ISOMERS

(71) Applicant: ExxonMobil Chemical Patents Inc., Baytown, TX (US)

(72) Inventors: Constantinos P. Bokis, The Woodlands, TX (US); Javier Guzman, Porter, TX (US); Monica D. Lotz, Houston, TX (US); Michael P. Lanci, Flemington, NJ (US); Catherine M. Dorsi, Houston, TX (US); Scott J. Weigel, Allentown, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/958,383

(22) PCT Filed: Jan. 8, 2019

(86) PCT No.: PCT/US2019/012621
§ 371 (c)(1),
(2) Date: Jun. 26, 2020

(87) PCT Pub. No.: WO2019/143495
PCT Pub. Date: Jul. 25, 2019

(65) Prior Publication Data
US 2021/0053890 A1 Feb. 25, 2021

Related U.S. Application Data

(60) Provisional application No. 62/619,966, filed on Jan. 22, 2018.

(51) Int. Cl.
*C07C 7/00* (2006.01)
*B01D 3/10* (2006.01)
(Continued)

(52) U.S. Cl.
CPC ............ *C07C 7/005* (2013.01); *B01D 3/10* (2013.01); *C07C 2/66* (2013.01); *C07C 2/74* (2013.01);
(Continued)

(58) Field of Classification Search
CPC .. C07C 15/14; C07C 13/28; C07C 7/13; C07C 2/74; C07C 5/10; C07C 5/367;
(Continued)

(56) References Cited

U.S. PATENT DOCUMENTS 2,976,266 A   3/1961   Lytton et al. ............... 260/75
3,766,093 A   10/1973  Chu ............................ 252/455
(Continued)

FOREIGN PATENT DOCUMENTS

EP   0 293 032       7/1993   ............ C01B 35/10
WO   WO1997/017290   5/1997   ............ C01B 33/38
WO   WO2015/112252   7/2015   ............ C07C 15/14

OTHER PUBLICATIONS

Izard, E. F. et al. (1952) "Effect of Chemical Structure on Physical Properties of Isomeric Polyesters," *Jrnl. of Polymer Sci.*, v.IX(1), pp. 35-39.
(Continued)

*Primary Examiner* — Sharon Pregler

(57) ABSTRACT

Processes are described for separating 3,4'- and 4,4'-dimethylbiphenyl from a mixture comprising at least 3,3'-, 3,4'- and 4,4'-dimethylbiphenyl. In the processes, the mixture is cooled to produce a crystallization product comprising at least of the 4,4'-dimethylbiphenyl from the feed mixture and a first mother liquor product. The first mother liquor product is distilled to produce a bottoms stream enriched in 4,4'-dimethylbiphenyl as compared with the first mother liquor product and an overhead stream deficient in 4,4'-dimethylbiphenyl as compared with the first mother liquor product.
(Continued)

The overhead stream is then cooled to produce a second crystallization product comprising at least part of the 3,4'-dimethylbiphenyl from the overhead stream and a second mother liquor product.

15 Claims, 7 Drawing Sheets

(51) Int. Cl.

| | | |
|---|---|---|
| C07C 2/66 | (2006.01) | |
| C07C 2/74 | (2006.01) | |
| C07C 5/10 | (2006.01) | |
| C07C 5/27 | (2006.01) | |
| C07C 5/367 | (2006.01) | |
| C07C 7/04 | (2006.01) | |
| C07C 7/14 | (2006.01) | |
| C07C 15/14 | (2006.01) | |

(52) U.S. Cl.
CPC .............. *C07C 5/10* (2013.01); *C07C 5/2729* (2013.01); *C07C 5/367* (2013.01); *C07C 7/04* (2013.01); *C07C 7/14* (2013.01); *C07C 15/14* (2013.01)

(58) Field of Classification Search
CPC ......... C07C 2/66; C07C 5/2729; C07C 7/005; C07C 7/04; C07C 7/14; C07C 2601/14; C07C 5/2732; C07C 2/68; C07C 2/76; C07C 51/285; C07C 67/08; C07C 67/39; C07C 69/76; C07C 69/78; C08K 5/10; C08K 3/013; C08K 5/0016; C08K 2201/014; C08K 3/10; C08K 5/101; C08K 5/103; C08K 5/12
See application file for complete search history.

(56) References Cited

U.S. PATENT DOCUMENTS

| | | | |
|---|---|---|---|
| 3,842,040 | A | 10/1974 | Browne et al. ................ 260/75 |
| 3,842,041 | A | 10/1974 | Browne et al. ................ 260/75 |
| 3,894,104 | A | 7/1975 | Chang et al. ................ 260/668 |
| 4,016,218 | A | 4/1977 | Haag et al. ................... 260/671 |
| 4,401,556 | A | 8/1983 | Bezman et al. ............. 208/111 |
| 4,439,409 | A | 3/1984 | Puppe et al. ................ 423/328 |
| 4,826,667 | A | 5/1989 | Zones et al. ................. 423/277 |
| 4,954,325 | A | 9/1990 | Rubin et al. ................. 423/328 |
| 4,959,450 | A | 9/1990 | Morris et al. ................ 528/272 |
| 5,138,022 | A | 8/1992 | Mang et al. ................. 528/272 |
| 5,236,575 | A | 8/1993 | Bennett et al. ............... 208/46 |
| 5,250,277 | A | 10/1993 | Kresge et al. ............... 423/329 |
| 5,362,697 | A | 11/1994 | Fung et al. .................... 502/71 |
| 6,077,498 | A | 6/2000 | Diaz Cabanas et al. ..... 423/702 |
| 9,085,669 | B2 | 7/2015 | Dakka et al. ............ C08K 5/101 |
| 9,464,166 | B2 | 10/2016 | Dakka et al. ......... C08G 63/185 |
| 9,556,087 | B2 | 1/2017 | Dakka et al. ........... C07C 5/367 |
| 9,580,572 | B2 | 2/2017 | Dakka et al. ............. C08K 5/12 |
| 9,663,417 | B2 | 5/2017 | Dakka et al. ............. C07C 2/74 |
| 10,081,593 | B2 * | 9/2018 | Dakka ................. C09D 127/06 |
| 10,138,176 | B2 * | 11/2018 | Lanci ................ B01J 20/28007 |
| 2015/0361011 | A1 | 12/2015 | Salciccioli et al. ........ C07C 6/06 |
| 2016/0176785 | A1 | 6/2016 | Salciccioli et al. ... C07C 5/2737 |
| 2018/0362860 | A1 | 12/2018 | McCarthy et al. .... C10G 45/12 |
| 2020/0262971 | A1 | 8/2020 | Liu et al. ............ C08G 63/199 |

OTHER PUBLICATIONS

Krigbaum, W. R. et al. (1982) "Aromatic Polyesters Forming Thermotropic Smectic Mesophases," *Jornl. of Polymer Sci.*, v.20(2), pp. 109-115.

Meurisse, P. et al. (1981) "Polymers with Mesogenic Elements and Flexible Spaces in the Main Chain: Aromatic-Aliphatic Polyesters," *British Polymer Journal*, v.13(2), pp. 55-63.

Mukhopdhyay, S. et al. (2000) "Tandem One-Pot Palladium-Catalyzed Reductive and Oxidative Coupling of Benzene and Chlorobenzene," *Jrnl. Org. Chem.*, v. 65(10), pp. 3107-3110.

\* cited by examiner

PRODUCTION AND USE OF 3,4' AND 4,4'-DIMETHYLBIPHENYL ISOMERS

CROSS-REFERENCE OF RELATED APPLICATIONS

This application is a § 371 National Phase entry of International Application No. PCT/US2019/012621 filed Jan. 08, 2019, which claims priority to U.S. Provisional Patent Application No. 62/619,966, filed Jan. 22, 2018, the disclosures of which are incorporated by reference.

FIELD

This disclosure relates to the production and use of 3,4' and 4,4'-dimethylbiphenyl isomers.

BACKGROUND

Dimethylbiphenyl (DMBP) compounds are useful intermediates in the production of a variety of commercially valuable products, including polyesters and plasticizers for PVC and other polymer compositions. For example, DMBP can readily be converted to an ester plasticizer by a process comprising oxidation of the DMBP to produce the corresponding mono- or dicarboxylic acid followed by esterification with a long chain alcohol. For certain uses, it is important to maximize the level of the 3,4'-isomer and particularly the 4,4'-isomer in the product.

In addition, 4,4'-biphenyl-dicarboxylic acid, optionally together with 3,4'-biphenyl-dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

For example, homopolyesters of 4,4'-biphenyl dicarboxylic acid (BPDA) and various aliphatic diols have been disclosed in the literature. For example, a homopolyester resulting from the reaction between 4,4'-biphenyl dicarboxylic acid and ethylene glycol was disclosed in the 9 JOURNAL OF POLYMER SCIENCE 35 (1952). And homopolyesters made from 4,4'-biphenyl dicarboxylic acid and a number of diols including ethylene glycol, 1,4-butanediol and 1,6-hexanediol were disclosed in 13 BRITISH POLYMER JOURNAL 57 (1981). Homopolyesters of 4,4'-biphenyl dicarboxylic acid and ethylene glycol were also disclosed in U.S. Pat. Nos. 3,842,040 and 3,842,041.

Copolyesters of 4,4'-biphenyl dicarboxylic acid and mixtures of aliphatic diols are also disclosed in for example in U.S. Pat. No. 2,976,266. Copolyesters from 4,4'-biphenyl dicarboxylic acid, and the mixtures of 1,4-cyclohexanedimethanol and 1,6-hexanediol are disclosed in U.S. Pat. No. 4,959,450. Copolyesters of 4,4'-biphenyl dicarboxylic acid and terephthalic acid, and certain aliphatic diols are disclosed for example in the 20 JOURNAL OF POLYMER SCIENCE, POLYM. LETTERS 109 (1982). U.S. Pat. No. 5,138,022 disclosed copolyesters of 3,4' biphenyl dicarboxylic acid and optionally 4,4'-biphenyl dicarboxylic acid, and certain aliphatic diols like ethylene glycol, 1,4-butanediol, and 1,4-cyclohexanedimethanol.

As disclosed in U.S. Pat. Nos. 9,580,572 and 9,663,417 DMBP compounds may be produced by hydroalkylation of toluene followed by dehydrogenation of the resulting (methylcyclohexyl)toluene (MCHT). However, even using a selective molecular sieve as catalyst for the hydroalkylation step, this process tends to yield a mixture of all six DMBP isomers, namely 2,2', 2,3', 2,4', 3,3', 3,4', and 4,4' DMBP, in which the 2,X' (where X' is 2', 3', or 4') and 3,3' DMBP isomer content may be 50% by weight or more of the total DMBP product.

Alternative routes via benzene are described in U.S. Pat. No. 9,085,669, in which the benzene is initially converted to biphenyl, either by oxidative coupling or by hydroalkylation to cyclohexyl benzene (CHB) followed by dehydrogenation of the CHB, and then the biphenyl is alkylated with methanol. Again, however, the alkylated product is a mixture of DMBP isomers, in which the levels of the desired 3,4' and 4,4' isomers may be lower than 50% by weight of the total DMBP product.

There is, therefore, interest in developing a process for producing dimethylbiphenyl compounds in which the yield of 3,4' isomer, and particularly the 4,4' isomer, is maximized.

For example WO 2015/112252 discloses a process for producing 3,4' and/or 4,4' dimethyl-substituted biphenyl compounds comprising: contacting a feed comprising toluene with hydrogen in the presence of a hydroalkylation catalyst to produce a hydroalkylation reaction product comprising (methylcyclohexyl)toluenes; dehydrogenating at least part of the hydroalkylation reaction product in the presence of a dehydrogenation catalyst to produce a dehydrogenation reaction product comprising a mixture of dimethyl-substituted biphenyl isomers; and separating the dehydrogenation reaction product into at least a first stream containing at least 50% of 3,4' and 4,4'-dimethylbiphenyl isomers by weight of the first stream and at least one second stream comprising one or more 2,X' (where X' is 2', 3', or 4') and 3,3' dimethylbiphenyldimethyl-1,1'-biphenyl isomers. The separation of the dehydrogenation reaction product into the first and second streams is conveniently effected by distillation, after which the first stream may be supplied to a crystallizer to separate a third stream rich in 4,4'-dimethylbiphenyl.

SUMMARY

According to the present disclosure, it has now been found that a unique combination of crystallization steps with an intermediate distillation step can be used to separate substantially pure 3,4'- and 4,4'-dimethylbiphenyl streams from a mixture of these isomers with at least 3,3'-dimethylbiphenyl. Feeding the remaining 3,3'-dimethylbiphenyl and optionally other DMBP isomers to an isomerization loop can then be employed to maximize the recovery of the desired 3,4'- and 4,4' compounds.

Thus, in one aspect, the present disclosure resides in a process for producing 3,4'- and 4,4'-dimethylbiphenyl, the process comprising:

(a) cooling a feed mixture comprising at least 3,3'-, 3,4'- and 4,4'-dimethylbiphenyl to produce (i) a first crystallization product comprising at least part of the 4,4'-dimethylbiphenyl from the feed mixture, and (ii) a first mother liquor product;

(b) distilling at least part of the first mother liquor product to produce a bottoms stream enriched in 4,4'-dimethylbiphenyl as compared with the first mother liquor product and an overhead stream depleted in 4,4'-dimethylbiphenyl as compared with the first mother liquor product; and (c) cooling at least part of the overhead stream to a second temperature to produce (i) a second crystallization product comprising at least part of the 3,4'-dimethylbiphenyl from the overhead stream, and (ii) a second mother liquor product.

Typically, the cooling step (a) comprises cooling the feed mixture to a first temperature from −30 to 40° C., such as from −6 to 40° C. Additionally or alternatively, the cooling step (c) typically comprises cooling the at least part of the overhead stream to a second temperature of less than −6° C. In any aspect, the process often further comprises recycling at least part of the bottoms stream to the cooling step (a).

In another aspect, the present disclosure relates to a system comprising:

(a) a first crystallizer adapted to receive a feed mixture comprising at least 3,3'-, 3,4'- and 4,4'-dimethylbiphenyl and produce (i) a first crystallization product comprising at least part of the 4,4'-dimethylbiphenyl from the feed mixture, and (ii) a first mother liquor product;

(b) a first distillation column in fluid communication with the first crystallizer, wherein the distillation column is adapted to receive at least part of the first mother liquor product and produce a bottoms stream enriched in 4,4'-dimethylbiphenyl as compared with the first mother liquor product and an overhead stream depleted in 4,4'-dimethylbiphenyl as compared with the first mother liquor product; and (c) a second crystallizer in fluid communication with the distillation column, wherein the second crystallizer is adapted to receive at least part of the overhead stream and produce (i) a second crystallization product comprising at least part of the 3,4'-dimethylbiphenyl from the overhead stream, and (ii) a second mother liquor product.

In another aspect, the present disclosure relates to a process for producing 3,4' and 4,4' dimethylbiphenyl, the process comprising:

(a) contacting toluene with hydrogen in the presence of a hydroalkylation catalyst under conditions effective to produce a hydroalkylation product comprising (methylcyclohexyl)toluenes;

(b) dehydrogenating at least part of the hydroalkylation reaction product in the presence of a dehydrogenation catalyst under conditions effective to produce a dehydrogenation reaction product comprising a mixture of dimethyl-substituted biphenyl isomers, wherein the mixture of dimethyl-substituted biphenyl isomers comprises at least 3,3'-, 3,4'- and 4,4'-dimethylbiphenyl;

(c) cooling at least part of the dehydrogenation reaction product to produce (i) a first crystallization product comprising at least part of the 4,4'-dimethylbiphenyl from the dehydrogenation reaction product, and (ii) a first mother liquor product;

(d) distilling at least part of the first mother liquor product to produce a bottoms stream enriched in 4,4'-dimethylbiphenyl as compared with the first mother liquor product and an overhead stream depleted in 4,4'-dimethylbiphenyl as compared with the first mother liquor product; and (e) cooling at least part of the overhead stream to produce (i) a second crystallization product comprising at least part of the 3,4'-dimethylbiphenyl from the overhead stream, and (ii) a second mother liquor product.

DETAILED DESCRIPTION OF THE PREFERRED EMBODIMENTS

Figure 1:
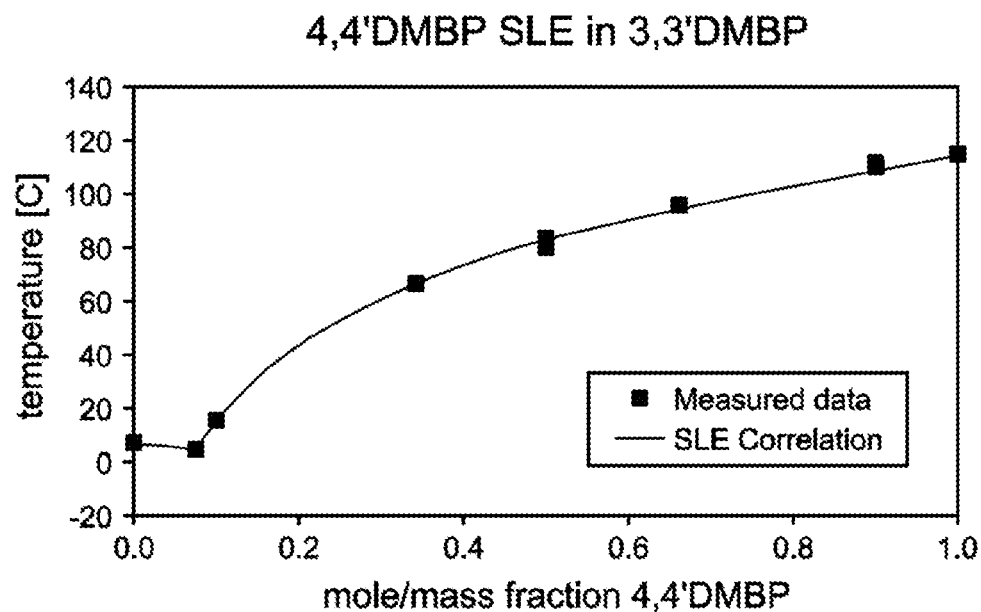
FIG. 1 is a graph comparing the results of solid-liquid equilibrium (SLE) experiments and computer modeling of the solubility and precipitation behavior of 4,4'-dimethylbiphenyl in a binary mixture with 3,3'-dimethylbiphenyl.
Figure 2:
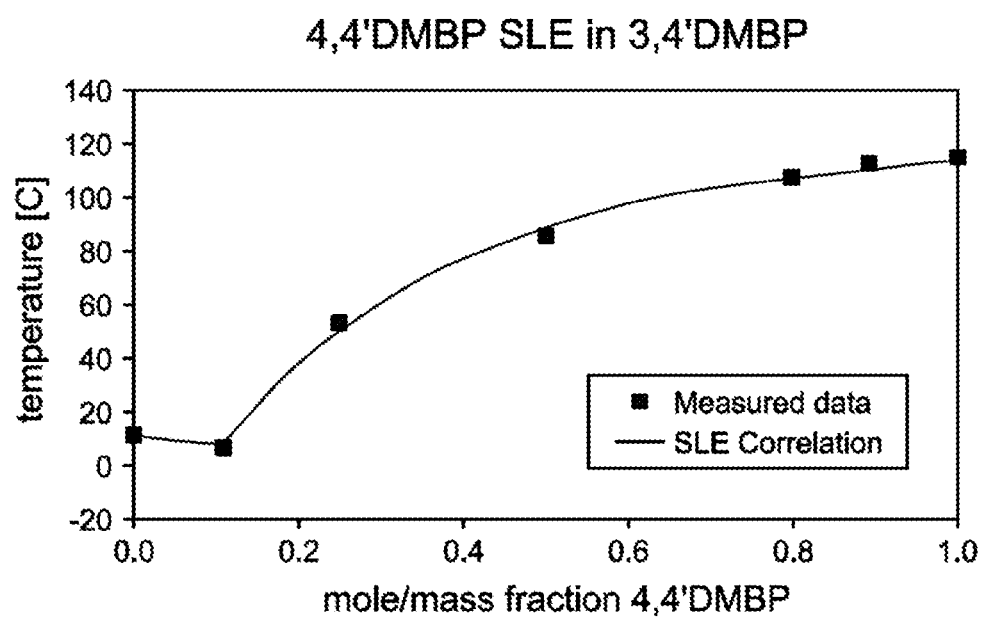
FIG. 2 is a graph comparing the results of SLE experiments and computer modeling of the solubility and precipitation behavior of 4,4'-dimethylbiphenyl in a binary mixture with 3,4'-dimethylbiphenyl.

Described herein are processes and systems of producing dimethyl-substituted biphenyl compounds, particularly from low cost feeds, such as toluene and/or benzene, and for optimizing recovery of the 3,4' and 4,4'-isomers by a combination of distillation and multiple crystallization steps, optionally with isomerization or hydrogenation/transalkylation of the 3,3' and other DMBP isomers to enhance the overall yield of the 3,4' and 4,4'-isomers.

As used herein, the term dimethylbiphenyl (DMBP) refers to compounds having the general chemical structure:

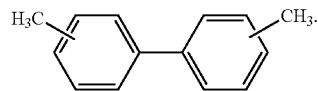

Production of Dimethylbiphenyl Compounds from Toluene

Often, the feed employed in the present processes comprises toluene, which is initially converted to (methylcyclohexyl)toluenes by reaction with hydrogen over a hydroalkylation catalyst according to the following reaction:

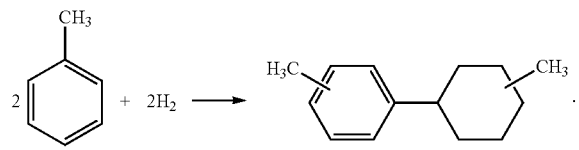

The catalyst employed in the hydroalkylation reaction is generally a bifunctional catalyst comprising a hydrogenation component and a solid acid alkylation component, typically a molecular sieve. The catalyst may also include a binder such as clay, alumina, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between 0.05 and 10 wt %, such as between 0.1 and 5 wt %, of the catalyst.

Often, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Alternatively, the solid acid alkylation component preferably comprises a molecular sieve of the MCM-22 family The term "MCM-22 family material" (or "material of the MCM-22 family" or "molecular sieve of the MCM-22 family"), as used herein, includes one or more of: molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference); molecular sieves made from a common second degree building block, being a 2-dimensional tiling of such MWW framework topology unit cells, forming a monolayer of one unit cell thickness, preferably one c-unit cell thickness; molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstroms. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032 A1), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and hydrogen, the feed to the hydroalkylation reaction may include benzene and/or xylene which can undergo hydroalkylation to produce various methylated cyclohexylbenzene molecules of $C_{12}$ to $C_{16}$ carbon number. A diluent, which is substantially inert under hydroalkylation conditions, may also be included in the hydroalkylation feed. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between 100° C. and 400° C., such as between 125° C. and 250° C., while suitable reaction pressures are between 100 and 7,000 kPa, such as between 500 and 5,000 kPa. The molar ratio of hydrogen to aromatic feed is typically from 0.15:1 to 15:1.

In the present process, it is found that MCM-22 family molecular sieves are particularly active and stable catalysts for the hydroalkylation of toluene or xylene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise: at least 60 wt %, such as at least 70 wt %, for example at least 80 wt % of the 3,3', 3,4', 4,3' and 4,4'-isomers of (methylcyclohexyl)toluene based on the total weight of all the (methylcyclohexyl)toluene isomers; less than 40 wt %, such as less than 30 wt %, for example from 15 to 25 wt % of the 2,2', 2,3', and 2,4'-isomers of (methylcyclohexyl)toluene based on the total weight of all the (methylcyclohexyl)toluene isomers; less than 30 wt % of methylcyclohexane and less than 2% of dimethylbicyclohexane compounds; and less than 1 wt % of compounds containing in excess of 14 carbon atoms, such as di(methylcyclohexyl)toluene.

The hydroalkylation reaction product may also contain significant amounts of residual toluene, for example up to 50 wt %, such as up to 90 wt %, typically from 60 to 80 wt % of residual toluene based on the total weight of the hydroalkylation reaction product. The residual toluene can readily be removed from the reaction effluent by, for example, distillation. The residual toluene can then be recycled to the hydroalkylation reactor, together with some or all of any unreacted hydrogen. In some embodiments, it may be desirable to remove the $C_{14+}$ reaction products, such as di(methylcyclohexyl)toluene, for example, by distillation.

The remainder of the hydroalkylation reaction effluent, composed mainly of (methylcyclohexyl)toluenes, is then dehydrogenated to convert the (methylcyclohexyl)toluenes to the corresponding methyl-substituted biphenyl compounds. The dehydrogenation is conveniently conducted at a temperature from 200° C. to 600° C. and a pressure from 100 kPa to 3550 kPa (atmospheric to 500 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In one embodiment, the Group 10 element is present in an amount from 0.1 to 5 wt % of the catalyst. In some cases, the dehydrogenation catalyst may also include tin or a tin compound to improve the selectivity to the desired methyl-substituted biphenyl product. In one embodiment, the tin is present in an amount from 0.05 to 2.5 wt % of the catalyst.

Particularly using an MCM-22 family-based catalyst for the upstream hydroalkylation reaction, the product of the dehydrogenation step comprises dimethylbiphenyl compounds in which the concentration of the 3,3'-, 3,4'- and 4,4' isomers is at least 50 wt %, such as at least 60 wt %, for example at least 70 wt % based on the total weight of dimethylbiphenyl compounds. Typically, the concentration of the 2,X'-dimethylbiphenyl isomers in the dehydrogenation product is less than 50 wt %, such as less than 30 wt %, for example from 5 to 25 wt % based on the total weight of dimethylbiphenyl compounds.

Production of Dimethylbiphenyl Compounds from Benzene

In other aspects, the present processes for producing dimethylbiphenyl compounds employ benzene as the feed and comprises initially converting the benzene to biphenyl. For example, benzene can be converted directly to biphenyl by reaction with oxygen over an oxidative coupling catalyst as follows:

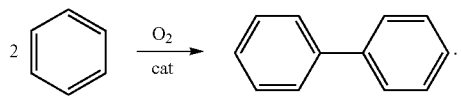

Details of the oxidative coupling of benzene can be found in Ukhopadhyay, Sudip; Rothenberg, Gadi; Gitis, Diana; Sasson, Yoel, Casali Institute of Applied Chemistry, Hebrew University of Jerusalem, Israel, 65(10) JOURNAL OF ORGANIC CHEMISTRY 3107-3110 (2000), incorporated herein by reference.

Alternatively, benzene can be converted to biphenyl by hydroalkylation to cyclohexylbenzene according to the reaction:

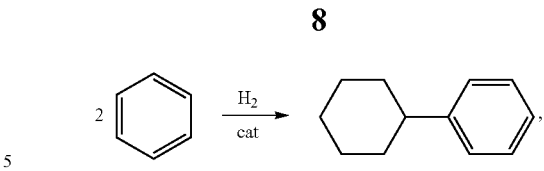

followed by dehydrogenation of the cyclohexylbenzene as follows:

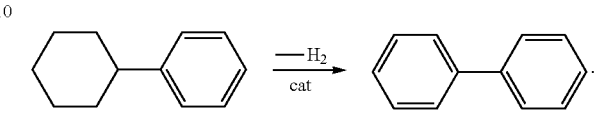

In such a process, the benzene hydroalkylation can be conducted in the same manner as described above for the hydroalkylation of toluene, while the dehydrogenation of the cyclohexylbenzene can be conducted in the same manner as described above for the dehydrogenation of (methylcyclohexyl)toluene.

Alternatively, benzene can be converted to biphenyl via thermal dehydrocondensation (i.e., contacting with heat), optionally conducted in the presence of steam. Direct dehydrocondensation of benzene to bipheneyl is further described in Thompson, Q. E., Biphenyl and Terphenyls, Kirk-Othmer Encyclopedia of Chemical Technology (2000).

In any case, the biphenyl product of the oxidative coupling step, dehydrocondensation, or the hydroalkylation/dehydrogenation sequence is then methylated, for example with methanol, to produce dimethylbiphenyl. Any known alkylation catalyst can be used for the methylation reaction, such as an intermediate pore molecular sieve having a Constraint Index (as defined in U.S. Pat. No. 4,016,218) of 3 to 12, for example ZSM-5.

The composition of the methylated product will depend on the catalyst and conditions employed in the methylation reaction, but inevitably will comprise a mixture of the different isomers of dimethylbiphenyl. Typically, the methylated product will contain from 50 to 100 wt % of 3,3'-, 3,4'- and 4,4' dimethylbiphenyl isomers and from 0 to 50 wt % of 2,X' (where X' is 2', 3' or 4')-dimethylbiphenyl isomers based on the total weight of dimethylbiphenyl compounds in the methylation product.

Separation of 3,4' and 4,4'-Dimethylbiphenyl Isomers

The present processes provide a simple and effective method of separately isolating and recovering the 3,4' and 4,4' dimethylbiphenyl isomers from the products of the reaction sequences described above. In addition, as will be discussed below, in some aspects the present processes provide for conversion of some or all the remaining 2,X' (where X' is 2', 3' or 4') and 3,3'-dimethylbiphenyl isomers into the more desirable 3,4' and 4,4' dimethylbiphenyl isomers.

Irrespective of the process used, the raw dimethylbiphenyl product from the production sequences described will contain unreacted components and by-products in addition to a mixture of dimethylbiphenyl isomers. For example, where the initial feed comprises toluene and the production sequence involves hydroalkylation to MCHT and dehydrogenation of the MCHT, the raw dimethylbiphenyl product will tend to contain residual toluene and MCHT and by-products including hydrogen, methylcyclohexane dimethylcyclohexylbenzene, and $C_{14+}$ heavy hydrocarbons in addition to the target dimethylbiphenyl isomers. Thus, often, prior to any separation of the dimethylbiphenyl isomers, the raw product of the MCHT dehydrogenation is subjected to one or more initial separation steps to remove at least part of the residues and by-products with significantly different boiling points from the desired to dimethylbiphenyl isomers. In alternative aspects, such initial separation steps may be omitted, particularly in aspects where the initial feed comprises benzene. In such aspects, the raw dimethylbiphenyl product may be provided directly to the single or multi-stage crystallization/distillation system described herein.

For example, the hydrogen by-product can be removed in a vapor/liquid separator and recycled to the hydroalkylation and/or MCHT dehydrogenation steps. The remaining liquid product can then be fed to one or more distillation columns to remove residual toluene and methylcyclohexane by-product, as well as effect initial separation of some of the lower boiling DMBP isomers. Thus, the normal boiling points and melting points of the dimethylbiphenyl isomers are shown in Table 1 below.

TABLE 1

| Isomer | Normal Boiling Point (° C.) | Melting Point (° C.) |
| --- | --- | --- |
| 2,2'-Dimethylbiphenyl | 260.70 | — |
| 2,3'-Dimethylbiphenyl | 271.50 | — |
| 2,4'-Dimethylbiphenyl | 275.26 | −23.67 |
| 3,3'-Dimethylbiphenyl | 289.27 | 8.00 |
| 3,4'-Dimethylbiphenyl | 292.87 | 11.55 |
| 4,4'-Dimethylbiphenyl | 295.66 | 114.77 |

From Table 1 it will be seen that the similarity of the boiling points of the 3,3', 3,4' and 4,4' DMBP isomers precludes their effective separation by distillation. However, the 2,X' (where X' is 2', 3' or 4') isomers all have boiling points at least 15° C. below the 3,3', 3,4' and 4,4' isomers and so can be readily separated from the latter by distillation. Thus, in certain aspects of the present processes, the liquid product of the MCHT dehydrogenation step is supplied to a distillation unit where the toluene is removed as overhead for recycle to the hydroalkylation unit, the unreacted MCHT and 2,X'-DMBP isomers are removed as an intermediate stream and the 3,3', 3,4' and 4,4' DMBP isomers and heavy ($C_{14+}$) by-products are separated as a bottoms stream. This bottoms stream can then be supplied to a further distillation column to remove the 3,3', 3,4' and 4,4' DMBP isomers for recovery of at least the 3,4' and 4,4' DMBP isomers, while the heavies are conveniently purged from the system. A typical 3,3', 3,4' and 4,4' DMBP isomer mixture obtained from such a multi-stage distillation process would have the following composition by weight.

3,3'-dimethylbiphenyl: 25%
3,4'-dimethylbiphenyl: 55%
4,4'-dimethylbiphenyl: 20%

It will be seen from Table 1 that crystallization provides a much more attractive option than distillation for the separation of the 3,3', 3,4' and 4,4' DMBP isomers from a ternary mixture such as that listed above because there is a significant variation in the melting points of these isomers. The 4,4'-DMBP isomer has a much higher melting point than all other isomers, and it will be the first one that will precipitate as pure solid in a crystallizer. The next higher melting point belongs to 3,4'-DMBP, but it's only 3.5° C. higher that then next higher melting point, that of 3,3'-DMBP. Solid-liquid equilibrium (SLE) lab experiments were performed to investigate the solubility and precipitation behavior of each of the isomers of interest in this process. In addition, a first-principles thermodynamic SLE model and computer algorithm has been assembled to describe and make useful predictions for the SLE behavior. The model uses the ideal solubility expression for each isomer, based on the melting temperature and heat of fusion of each species, and is adjusted for non-ideal solubility behavior, quantified by the experimental SLE measurements and an activity coefficient model (NRTL).

Figure 3:
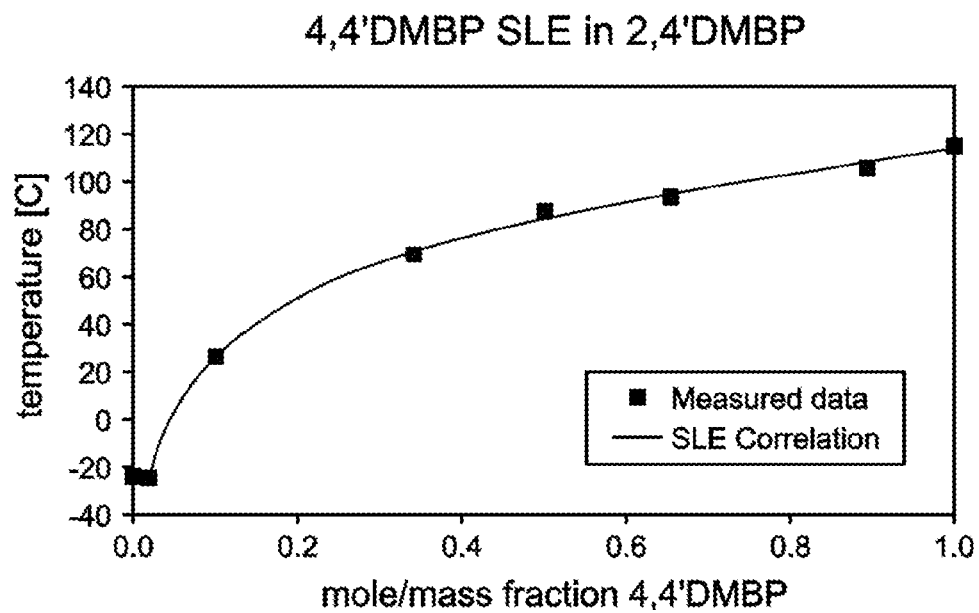
FIG. 3 is a graph comparing the results of SLE experiments and computer modeling of the solubility and precipitation behavior of 4,4'-dimethylbiphenyl in a binary mixture with 2,4'-dimethylbiphenyl.
Figure 4:
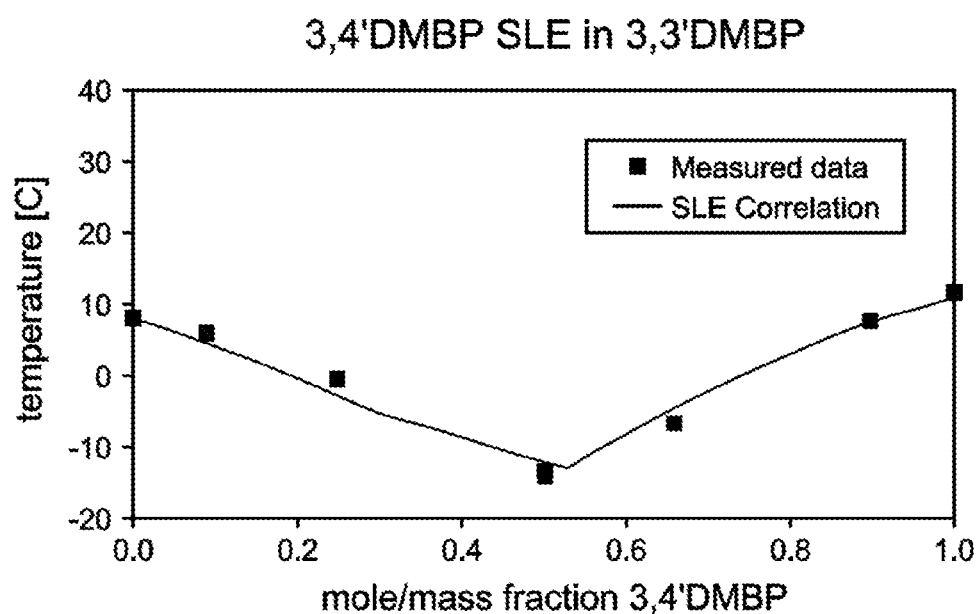
FIG. 4 is a graph comparing the results of solid-liquid equilibrium (SLE) experiments and computer modeling of the solubility and precipitation behavior of 3,4'-dimethylbiphenyl in a binary mixture with 3,3'-dimethylbiphenyl.

The graphs in FIGS. 1 to 4 show the SLE measurements and model correlation for various binary systems. These graphs plot the equilibrium solubility of one isomer in another as function of temperature. For example, the graph in FIG. 1 shows the equilibrium solubility of 4,4'-dimethylbiphenyl in 3,3'-dimethylbiphenyl. As shown in FIG. 1, the following observations can be made. A binary solution of 4,4'-dimethylbiphenyl in 3,3'-dimethylbiphenyl that comprises almost 100% 4,4'-dimethylbiphenyl starts to form solid 4,4'-dimethylbiphenyl at a temperature of 114.77° C. (the melting temperature of 4,4'-dimethylbiphenyl). A binary solution comprising 50:50 3,3'-dimethylbiphenyl and 4,4'-dimethylbiphenyl starts to form solid 4,4'-dimethylbiphenyl 1 at a temperature of 83° C. A binary solution that is 7.5 wt % 4,4'-dimethylbiphenyl remains in the liquid phase until cooled to 5° C., representing the eutectic point for the binary solution of 3,3'-dimethylbiphenyl and 4,4'-dimethylbiphenyl, below which temperature both 3,3'-dimethylbiphenyl and 4,4'-dimethylbiphenyl begin to precipitate as solids. Very similar behavior is observed for 4,4'-dimethylbiphenyl in 3,4'-dimethylbiphenyl (FIG. 2) and 4,4'-dimethylbiphenyl in 2,4'-dimethylbiphenyl (FIG. 3). In the case of 3,4'-dimethylbiphenyl in 3,3'-dimethylbiphenyl (FIG. 4), the eutectic point is located at −14° C., and the liquid mixture at the eutectic point is close to 50:50 concentration. As seen from FIGS. 1 to 4, the predicted values generated from the first-principles thermodynamic SLE model and computer algorithm exhibit a high degree of correlation with all these binary systems.

Figure 5:
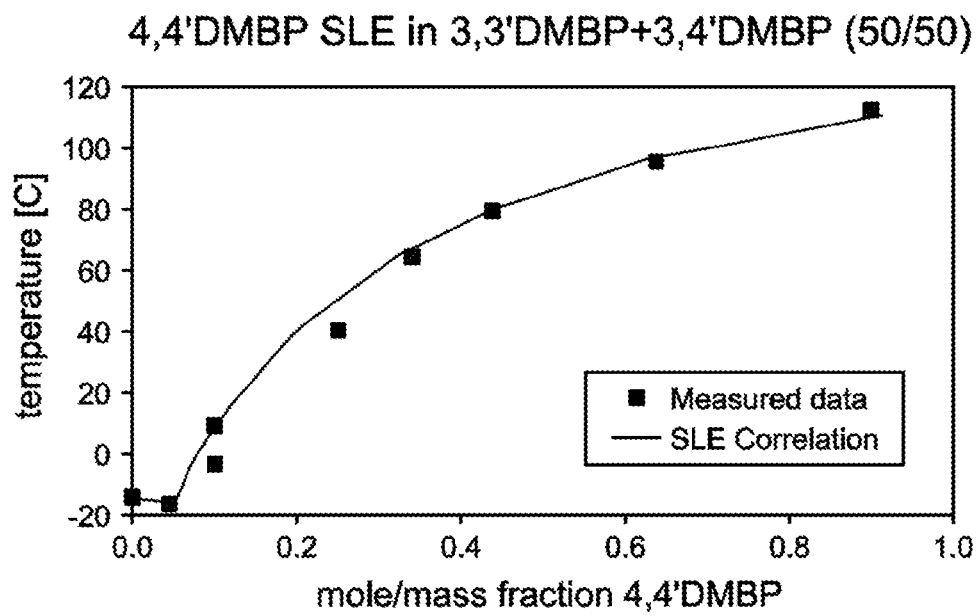
FIG. 5 is a graph comparing SLE model predictions with measured laboratory data for the solubility of 4,4'-dimethylbiphenyl in a 50:50 mixture of 3,3'-dimethylbiphenyl+3,4'-dimethylbiphenyl.

The graph in FIG. 5 shows the SLE measurements and model correlation for multi-component mixtures. In the graph, the SLE model predictions are compared with measured to laboratory data for the solubility of 4,4'-dimethylbiphenyl in a 50:50 mixture of 3,3'-dimethylbiphenyl+3,4'-dimethylbiphenyl. As seen in FIG. 5, the high degree of correlation between the predicted values from the SLE model and the measured values holds with extension from a binary to a ternary mixture.

Figure 6:
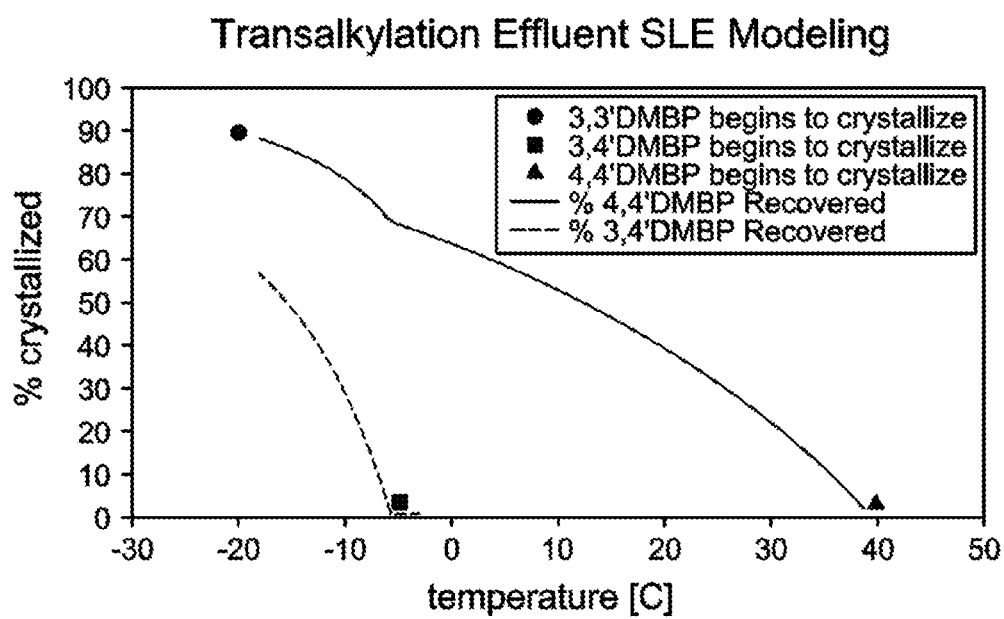
FIG. 6 is a graph showing the predicted amount of crystallization of 3,4' and 4,4'-dimethylbiphenyl with temperature from a ternary mixture with 3,3'-dimethylbiphenyl.

FIG. 6 provides a graph using the SLE model to predict the precipitation behavior of a ternary mixture of 3,3', 3,4' and 4,4' DMBP isomers from a single crystallizer, wherein the ternary mixture has the following composition by weight: 25% 3,3'-dimethylbiphenyl; 55% 3,4'-dimethylbiphenyl; and 20% 4,4'-dimethylbiphenyl. As shown in FIG. 6, all isomers remain dissolved in solution at temperatures higher than 40° C. Between 40 and −6° C., pure 4,4'-dimethylbiphenyl precipitates; and at −6° C., 70% of the 4,4'-dimethylbiphenyl is precipitated as solid and can be removed. Below −6° C., 3,4'-dimethylbiphenyl also begins to crystallize, together with 4,4'-dimethylbiphenyl which continues to crystallize. In this scheme, from a ternary mixture having this composition, 4,4'-dimethylbiphenyl can be separated in pure form at temperatures between 40 and −6° C.; however, 3,4'-dimethylbiphenyl cannot be separated in pure form. 3,3'-Dimethylbiphenyl begins to precipitate at −20° C. It should be recognized for purposes of this disclosure that the lowest temperature at which pure 4,4'-dimethylbiphenyl precipitates, i.e., the lowest temperature 3,4'-dimethylbiphenyl begins to co-precipitate, will vary based on the proportion of each isomer in the starting mixture. For example, this temperature may be as low as −30° C., or −20° C.

While the boiling points of the dimethylbiphenyl isomers are too close for separation via distillation, it has now been found that there is some variability that can be exploited for the benefit of separating pure 3,4'-dimethylbiphenyl, in addition to separating pure 4,4'-dimethylbiphenyl, from a mixture of at least the 3,4' and 4,4'-isomers. Thus, in the separation scheme of the present invention, after recovery of a first crystallization product comprising precipitated 4,4'-dimethylbiphenyl in a first crystallization unit, typically at a temperature of −30 to 40° C., preferably −20 to 40° C., more preferably −6 to 40° C., and more preferably −5 to 5° C., the remaining 4,4'-depleted mixture, i.e., the mother liquor, is supplied to a distillation column, which conveniently operates at low pressure (e.g., 20 mmHg) and high reflux ratio (e.g., 8-10) to enhance partition of 4,4'-dimethylbiphenyl. The column bottoms stream is rich in 4,4'-dimethylbiphenyl and is recycled back to the first crystallizer. The overhead stream of the column is typically fed to a second crystallization unit (2), typically at a temperature of less than −6° C., such as −17 to −14° C., where a second crystallization product comprising precipitated 3,4'-dimethylbiphenyl is collected. Depending on the composition of the initial DMBP isomer mixture, the mother liquor from the second crystallizer can be processed further by an isomerization unit, as described in more detail below, and recycled to a further distillation column upstream of the first crystallization unit. The further distillation column may be used to remove the undesired products of the isomerization unit, before processing through the first crystallization unit.

In any embodiment, the crystallization product from the first crystallization unit typically comprises greater than 75 wt % 4,4'-dimethylbiphenyl based on the weight of the crystallization product, such as greater than 90 wt % 4,4'-dimethylbiphenyl, or greater than 95 wt % 4,4'-dimethylbiphenyl, such as greater than 99 wt % 4,4'-dimethylbiphenyl, or even 100 wt % 4,4'-dimethylbiphenyl. Additionally or alternatively, the crystallization product from the first crystallization unit typically comprises less than 10 wt % 3,4'-dimethylbiphenyl based on the weight of the crystallization product, such as less than 5 wt % 3,4'-dimethylbiphenyl, or less than 1 wt % 3,4'-dimethylbiphenyl. In any embodiment, the crystallization product from the second crystallization unit typically comprises greater than 75 wt % 3,4'-dimethylbiphenyl based on the weight of the crystallization product, such as greater than 90 wt % 3,4'-dimethylbiphenyl, or greater than 95 wt % 3,4'-dimethylbiphenyl, such as greater than 99 wt % 3,4'-dimethylbiphenyl, or even 100 wt % 3,4'-dimethylbiphenyl.

Conversion of 2,X and 3,3'-Dimethylbiphenyl Isomers

In some embodiments of the present process, it may be desirable to convert at least part of the 2,X and 3,3'-dimethylbiphenyl isomers inherently produced from the benzene and/or toluene feedstocks to their 3,4' and/or 4,4' counterparts so that the yield of the latter can be maximized.

For example, as discussed above, after multi-stage crystallization of 3,4'- and 4,4'-dimethylbiphenyl from a mixture of 3,3'-, 3,4'- and 4,4'-dimethylbiphenyl isomers, the remaining 3,3'-DMBP rich mother liquor from the final crystallization stage can be supplied to an isomerization unit to convert the mother liquor back to an equilibrium distribution of DMBP isomers. Any acid catalyst can be used to effect isomerization of the dialkylbiphenyl compounds in the mother liquor. In most embodiments, the catalyst is a heterogeneous solid acid catalyst, such as a metal oxide, a clay or, more preferably, a molecular sieve. Particularly suitable molecular sieves are those having a Constraint Index (as defined in U.S. Pat. No. 4,016,218) less than 2, especially molecular sieves selected from the group consisting of BEA, FAU and MOR structure type molecular sieves and mixtures thereof.

The conditions used to effect isomerization of the dialkylbiphenyl-containing feed are not closely controlled, but suitably include a temperature from 100 to 450° C., such as 100 to 250° C., a pressure from 2 to 7,000 kPa-a, such as from 100 to 2000 kPa-a, and a WHSV from 0.2 to 20 $hr^{-1}$. In certain aspects, it may be desirable to select the temperature and pressure such as to maintain the dialkylbiphenyl components of the feed substantially in the liquid phase since this may reduce carbon losses resulting from cracking. More details of the isomerization process can be found in U.S. Publication No. 2016/176785, the entire contents of which are incorporated herein by reference.

Figure 7:
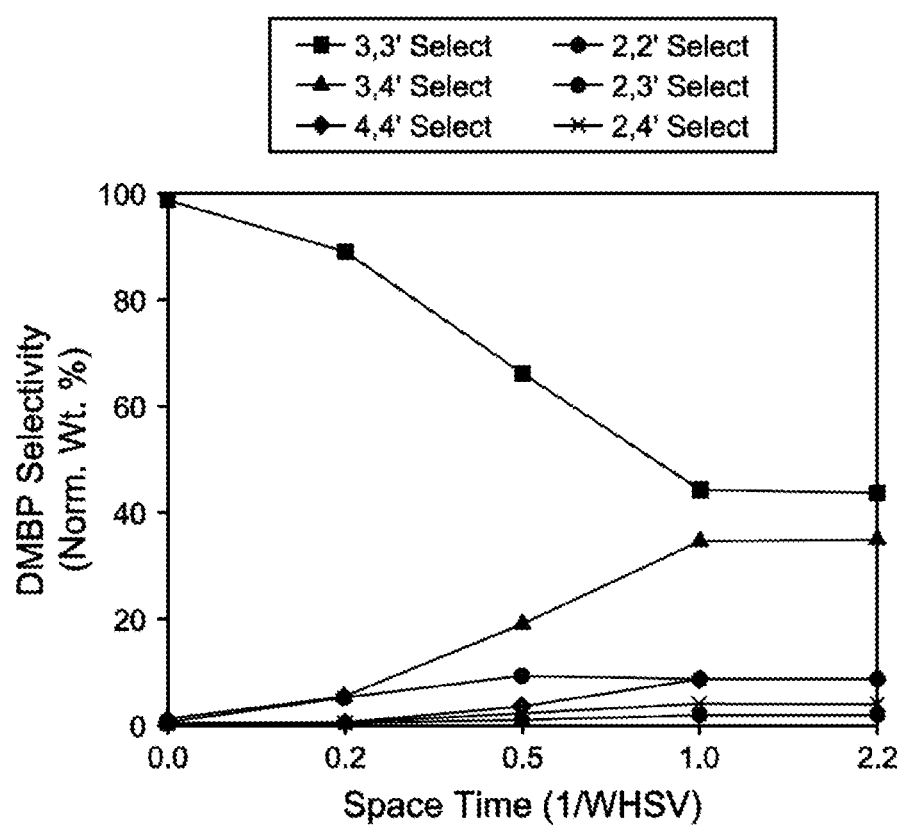
FIG. 7 is a graph showing the change in isomer distribution with weight hourly space velocity (WHSV) in the isomerization of 3,3'-dimethylbiphenyl over a USY catalyst at a temperature of 200° C.

One embodiment of a process for isomerizing 3,3'-DMBP over a USY catalyst at a temperature of 200° C. is illustrated in FIG. 7, from which it will be seen that higher selectivity for 3,4'- and 4,4'-DMBP was observed at WHSV≤1. Notably, selectivity leveled out at WHSV below 1, indicating thermodynamic equilibrium had been reached.

Additionally or alternatively, the mixture of 2,X'-DMBP isomers and unreacted MCHT removed by distillation of the raw DMBP product of the hydroalkylation/dehydrogenation process described above can be subjected to a three step process of (i) hydrogenation, followed by (ii) transalkylation and then (iii) dehydrogenation as described in the U.S. Publication No. 2015/361011, the entire contents of which are incorporated herein by reference. In this three step process, the hydrogenation (i) is conveniently conducted at a temperature of 50 to 400° C. in the presence of a metal or compound thereof from Groups 3, 4, 5, 6, 7, 8, 9, 10, 11 or 12 of the Periodic Table, especially Pt or Pd, metal to convert the 2,X'-DMBP isomers to the corresponding MCHT isomers. The hydrogenation effluent is then contacted with a transalkylation catalyst in the presence of toluene.

The transalkylation reaction can be conducted over a wide range of conditions but in most embodiments is effected at a temperature from 75 to 250° C., such as from 100 to 200° C., for example, 125 to 160° C. and a pressure from 100 to 3550 kPa-absolute, such as from 1000 to 1500 kPa-absolute. The reaction is normally conducted in the presence of a solid acid catalyst, such as a molecular sieve and in particular a molecular sieve having a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, ZSM-20, and mixtures thereof. Other suitable molecular sieves include molecular sieves of the MCM-22 family, including MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof. In particular, it is found that, as a result of steric issues, transalkylation favors the conversion of 2,X'-MCHT compounds to 3,Y' and 4,Y' (where Y' is 3' or 4')-MCHT compounds.

At least part of the transalkylation product is then catalytically dehydrogenated to produce a mixture of dialkylbiphenyl isomers including the 3,3'-, 3,4'- and 4,4'-isomers.

The catalyst employed in the dehydrogenation process is not critical but, often, comprises (i) an element or compound thereof from Group 10 of the Periodic Table of Elements, for example platinum, and (ii) tin or a compound of tin, both mounted on a refractory support, such as silica, alumina or carbon nanotubes. Suitable catalysts comprise a Group 10 element in an amount from 0.1 to 5 wt % of the catalyst and tin in an amount from 0.05 to 2.5 wt % of the catalyst. The dehydrogenation is conveniently conducted at a temperature from 200 to 600° C. and a pressure from 100 kPa-absolute to 3550 kPa-absolute (atmospheric to 500 psig). Optionally, the dehydrogenation is conducted in the same reactor as that used to dehydrogenate the product of the initial toluene hydroalkylation reaction. The invention will now be more particularly described with reference to FIGS. 8 through 10, which illustrate various non-limiting process configurations for the production and/or separation of 4,4'-dimethylbiphenyl or a mixture of 3,4'- and 4,4'-dimethylbiphenyl. It should be understood that certain process features, e.g., condensers, reboilers, reflux pumps, heat exchangers, additional recycle lines, etc. are not shown in the Figures, but could readily be incorporated into the illustrated process configurations by one of ordinary skill in the art.

Figure 8:
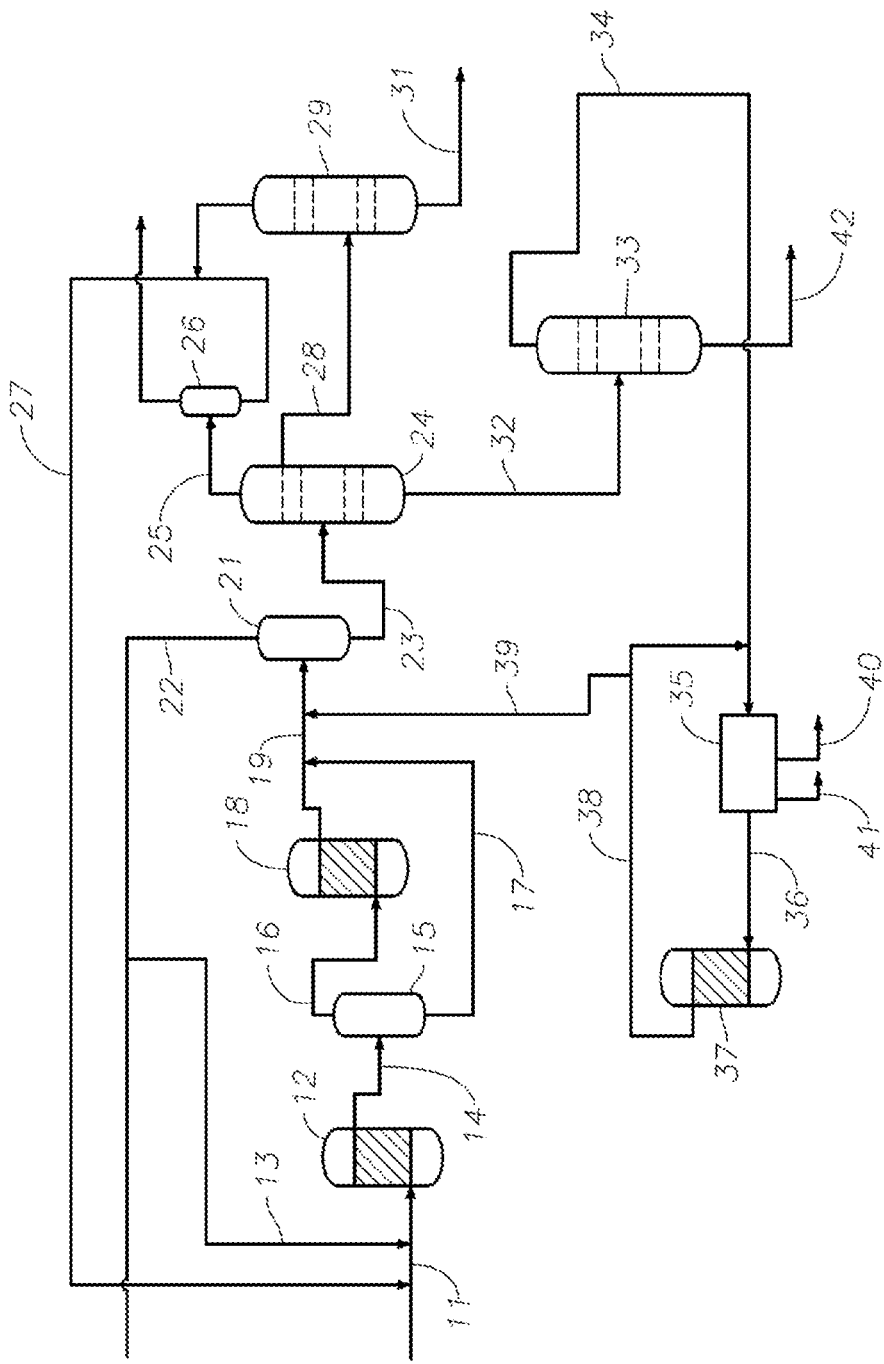
FIG. 8 is a flow diagram of a process according to one aspect of the present disclosure for producing 4,4' or a mixture of 3,4'- and 4,4'-dimethylbiphenyl from toluene.

One aspect of a process for producing 4,4' or a mixture of 3,4'- and 4,4'-dimethylbiphenyl which employs toluene as the aromatic feed and which includes isomerization of the 3,3'-dimethylbiphenyl by-product is shown in FIG. 8. In this aspect, fresh and recycled toluene is supplied by line 11 to a hydroalkylation reactor 12, which also receives make-up and recycled hydrogen via line 13. The hydroalkylation reaction product is removed from the reactor 12 via line 14 and fed to a condenser 15, where the product is divided into a gaseous fraction comprising (methylcyclohexyl)toluenes together with unreacted hydrogen and toluene and a liquid fraction comprising any $C_{14+}$ by-products. The gaseous fraction of the hydroalkylation reaction product is collected in line 16, while the liquid fraction is removed from the condenser 15 via line 17.

The gaseous fraction from the condenser 15 is fed by line 16 to a dehydrogenation reactor 18 where at least part of the (methylcyclohexyl)toluenes in the light fraction is converted to the corresponding dimethylbiphenyl isomers. The dehydrogenation reaction product is collected in line 19 and combined with the liquid fraction of the hydroalkylation reaction product in line 17 before the mixture is supplied to a gas/liquid separator 21, where hydrogen is removed via line 22 for recycle to the hydroalkylation reactor 12, and/or elsewhere in the process (not shown).

The liquid fraction exiting the gas/liquid separator 21 is a mixed stream comprising dimethylbiphenyl isomers, residual (methylcyclohexyl)toluenes, unreacted toluene and some $C_{14+}$ by-products and is fed by line 23 to a MCHT distillation column 24. The column 24 is operated to separate the mixed stream in line 23 into (i) an overhead stream containing most of the unreacted toluene, (ii) an intermediate stream containing a minor portion of the unreacted toluene, the residual (methylcyclohexyl)toluenes and most of the lower boiling dimethylbiphenyl isomers, namely the 2,X'-DMPB isomers, and (iii) a bottoms stream containing most of the lower boiling dimethylbiphenyl isomers, namely 3,3', 3,4' and 4,4'-DMBP, and the $C_{14+}$ by-products.

The overhead stream from the MCHT distillation column 24 is fed by line 25 to a toluene condenser 26, where any excess hydrogen and light hydrocarbons are removed and purged from the system, before the remaining toluene is recycled via line 27 to the hydroalkylation reactor 12.

The intermediate stream from the MCHT distillation column 24 is fed by line 28 to a further distillation column 29 where any remaining toluene is removed as overhead and combined with the toluene in recycle line 27. The bottoms from the column 29, composed mainly of residual (methylcyclohexyl)toluenes and most of the 2,X'-DMPB isomers, is collected in line 31 for further processing, typically in another unit of a larger petrochemical facility (not shown).

The bottoms stream from the MCHT distillation column 24 is fed by line 32 to a heavies column 33 where the $C_{14+}$ by-products in line 42 are removed and purged from the system and an overhead fraction rich in 3,3', 3,4' and 4,4'-DMBP is collected in line 34. The overhead fraction is supplied by line 34 initially to a single or multi-stage crystallization/distillation system 35 for separately recovering 4,4'-DMBP, and optionally 3,'4 DMBP, and then the remaining mother liquor, which is deficient in 3,4' and/or and 4,4'-DMBP, is supplied by line 36 to an isomerization reactor 37. Although the system 35 is shown in FIG. 8 as a single unit, in practice the actual system could optionally comprise at least the first and second crystallizers and the intermediate distillation column described above and shown, by way of example, in FIG. 10. The 4,4'-DMBP is collected in line 40, and optionally, 3,4'-DMBP is collected in line 41. The effluent from the isomerization reactor 37 has a higher concentration of 3,4' and 4,4'-DMBP isomers than the mother liquor in line 36 and is recycled via line 38 to the crystallization/distillation system 35 for recovery of additional 3,4' and/or 4,4'-DMBP. Optionally, a slip stream 39 can be removed from line 38 and fed to the separator 21 to allow eventual purging of any unwanted by-products generated by the isomerization reaction.

Figure 9:
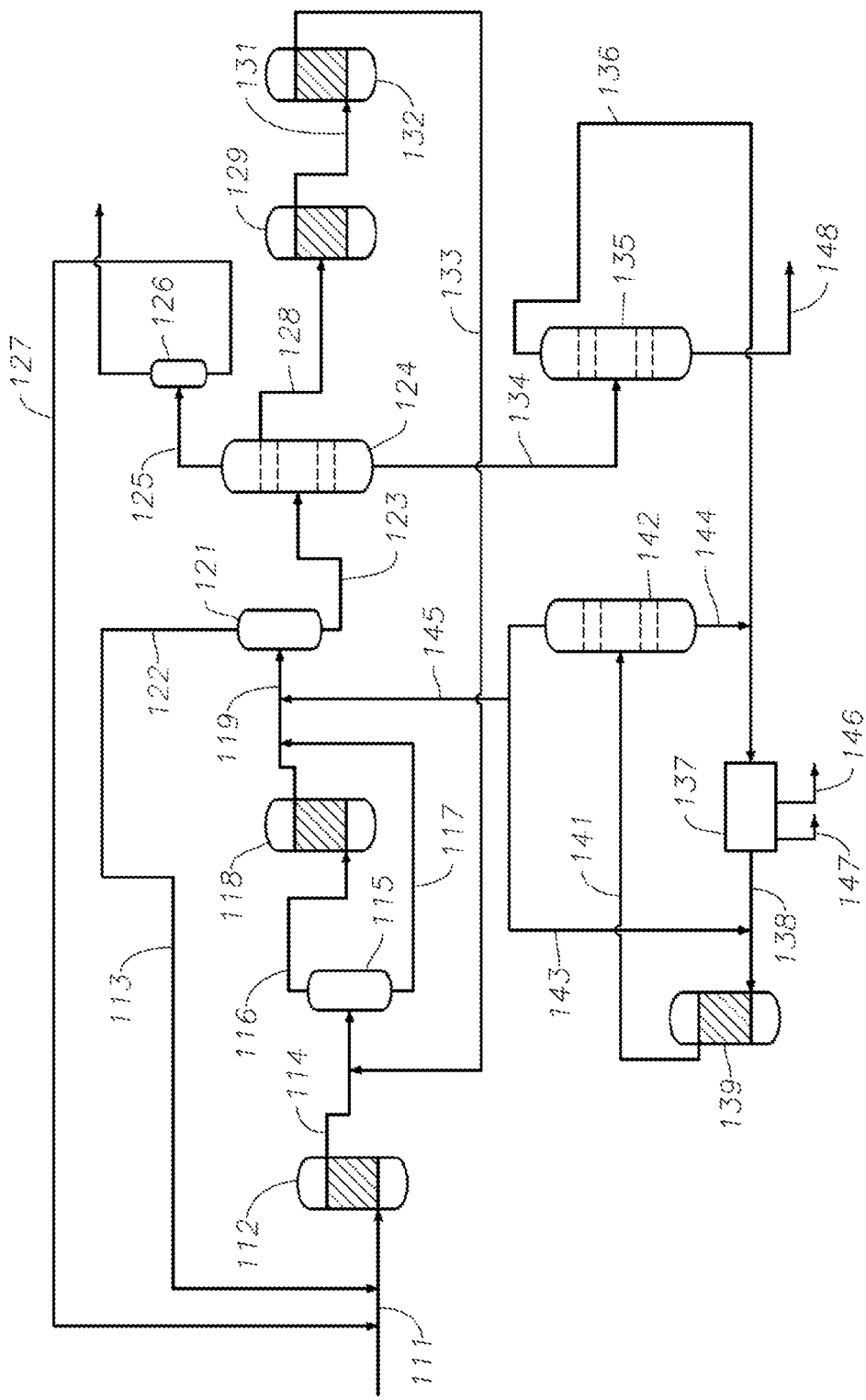
FIG. 9 is a flow diagram of a process according to a further aspect of the present disclosure for producing 4,4' or a mixture of 3,4'- and 4,4'-dimethylbiphenyl from toluene.

FIG. 9 discloses a further embodiment of a process for producing 4,4' or a mixture of 3,4'- and 4,4'-dimethylbiphenyl which again employs toluene as the aromatic feed and which includes isomerization of dimethylbiphenyl isomers not recovered via crystallization, e.g., 3,3'-dimethylbiphenyl, as well as hydrogenation/transalkylation/dehydrogenation of the 2,X'-dimethylbiphenyl and residual methyl(cyclohexyl)toluene component. In this embodiment, fresh and recycled toluene is supplied by line 111 to a hydroalkylation reactor 112, which also receives make-up and recycled hydrogen via line 113. The hydroalkylation reaction product is removed from the reactor 112 via line 114 and fed to a condenser 115, where the product is divided into a gaseous fraction comprising (methylcyclohexyl)toluenes together with unreacted hydrogen and toluene and a liquid fraction comprising any $C_{14+}$ by-products. The gaseous fraction of the hydroalkylation reaction product is collected in line 116, while the liquid fraction is removed from the condenser 115 via line 117.

The gaseous fraction from the condenser 115 is fed by line 116 to a dehydrogenation reactor 118 where at least part of the (methylcyclohexyl)toluenes in the light fraction is converted to the corresponding dimethylbiphenyl isomers. The dehydrogenation reaction product is collected in line 119 and combined with the liquid fraction of the hydroalkylation reaction product in line 117 before the mixture is supplied to a gas/liquid separator 121, where hydrogen is removed via line 122 for recycle to the hydroalkylation reactor 112 and/or elsewhere in the process (not shown).

The liquid fraction exiting the gas/liquid separator 121 is a mixed stream comprising dimethylbiphenyl isomers, residual (methylcyclohexyl)toluenes, unreacted toluene and some by-products and is fed by line 123 to a MCHT distillation column 124. The column 124 is operated to separate the mixed stream in line 123 into (i) an overhead stream containing at least a portion of the unreacted toluene, (ii) an intermediate stream containing at least a portion of the unreacted toluene, the residual (methylcyclohexyl)toluenes and most of the lower boiling dimethylbiphenyl isomers, namely the 2,X'-DMPB isomers, and (iii) a bottoms stream containing most of the lower boiling dimethylbiphenyl isomers, namely 3,3', 3,4' and 4,4'-DMBP, and the $C_{14+}$ by-products.

The overhead stream from the MCHT distillation column 124 is fed by line 125 to a toluene condenser 126, where any excess hydrogen and light hydrocarbons are removed and purged from the system, before the remaining toluene is recycled via line 127 to the hydroalkylation reactor 112.

The intermediate stream from the MCHT distillation column 124 is fed by line 128 to a hydrogenation reactor 129 in which the 1,X' and 2,X'-DMBP isomers in the intermediate stream are converted to the corresponding MCHT isomers. The effluent of the hydrogenation reactor 129 is then fed via line 131 to a transalkylation reactor 132, together with toluene, where 2,X'-MCHT and/or 1,X'-MCHT compounds in the hydrogenation effluent are selectively converted to 3,X'- and 4,X'-MCHT compounds. The transalkylation product is then recycled via line 133 to line 114 where it is combined with the effluent from the hydroalkylation reactor 112 before the combined stream is fed to the condenser 115 and then the dehydrogenation reactor 118.

The bottoms stream from the MCHT distillation column 124 is fed by line 134 to a heavies column 135 where the $C_{14+}$ by-products are removed via line 148 and purged from the system and an overhead fraction rich in 3,3', 3,4' and 4,4'-DMBP is collected in line 136. The overhead fraction is supplied by line 136 initially to a single or multi-stage crystallization/distillation system 137 for separately recovering 4,4'-DMBP, and optionally 3,4'-DMBP, and then the remaining mother liquor, which is deficient in 3,4' and/or 4,4'-DMBP, is supplied by line 138 to an isomerization reactor 139. Although the system 137 is shown in FIG. 9 as a single unit, in practice the actual system could optionally comprise at least the first and second crystallizers and the intermediate distillation column described above and shown, by way of example, in FIG. 10. The 4,4'-DMBP is collected in line 146, and optionally, 3,4'-DMBP is collected in line 147. The effluent from the isomerization reactor 139 has a higher concentration of 3,4' and 4,4'-DMBP isomers than the mother liquor in line 138 and is fed via line 141 to an isomerization column 142. The column 142 is operated so as to produce an overhead fraction which richer in 2,X'-DMBP isomers than the isomerization effluent and which is recycled via line 143 to the isomerization reactor 139 and a bottoms fraction which richer in 3,4' and 4,4'-DMBP than the isomerization effluent and which is fed via line 144 to the crystallization/distillation system 137. Optionally, a slip stream 145 can be removed from line 143 and fed to the separator 121 to allow eventual purging of any unwanted by-products generated by the isomerization reaction.

In a modification of the process shown in FIG. 9 (not shown), the isomerization column 142 is omitted and the effluent from the isomerization reactor 139 is recycled directly to the crystallization/distillation system 137.

Figure 10:
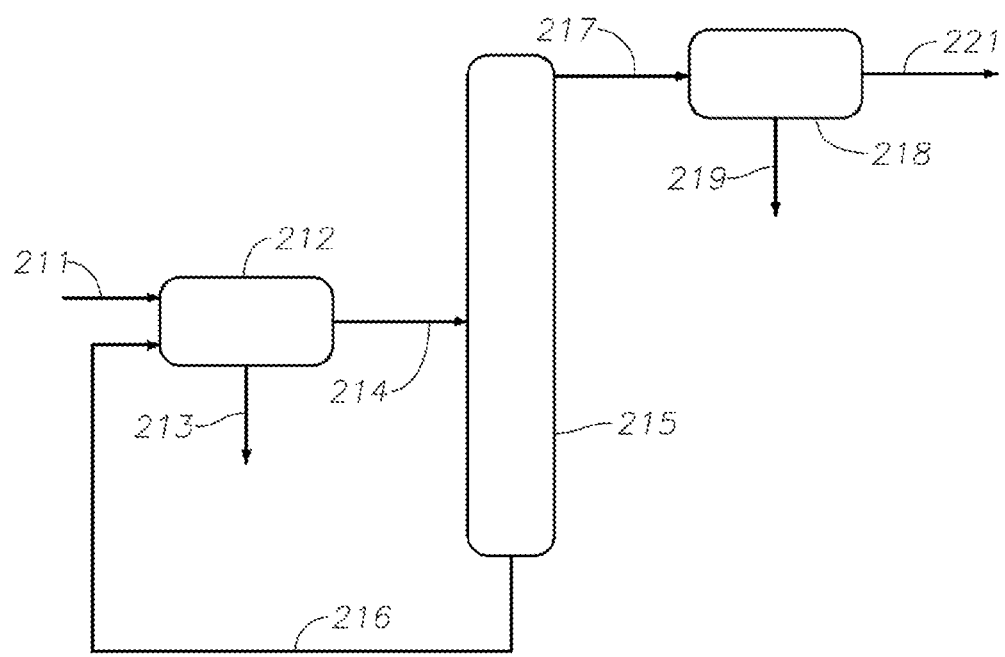
FIG. 10 is a flow diagram of a process according to one aspect of the present disclosure for separating 3,4'- and 4,4'-dimethylbiphenyl from a mixture of 3,3', 3,4'- and 4,4'-dimethylbiphenyl.

The invention will now be more particularly described with reference to the following non-limiting Example as illustrated by FIG. 10, in which a mixture of 3,3'-, 3,4'- and 4,4'-dimethylbiphenyl, such as that in line 34 in FIG. 8 and in line 136 in FIG. 9, is to be supplied via line 211 to a first crystallizer 212 operating at a first temperature such as to precipitate pure, solid 4,4'-dimethylbiphenyl from the mixture. The solid 4,4'-dimethylbiphenyl is recovered in line 213, while the remaining mother liquor is supplied via line 214 to a distillation column 215 which is operated to separate the mother liquor into bottoms stream rich in 4,4'-dimethylbiphenyl as compared to the mother liquor and an overhead stream rich in 3,3' and 3,4'-dimethylbiphenyl as compared to the mother liquor. The bottoms stream is recycled via line 216 back to the first crystallizer 212, while the overhead stream is fed by line 217 to a second crystallizer 218. The second crystallizer 218 is operated at a second temperature, often lower than the first temperature, such that pure, solid 3,4'-dimethylbiphenyl is precipitated from the overhead stream and recovered in line 219. The mother liquor remaining after recovery of the 3,4'-dimethylbiphenyl exits the second crystallizer 218 via line 221 and can be processed further, such as the isomerization reactor shown at 37 in FIG. 8 and at 139 in FIG. 9.

Example

In this Example a simulation was performed of the process shown in FIG. 10, in which the first crystallizer 212 was operated at a temperature of −5° C., the distillation column was operated at 20 mmHg and a reflux ratio of 8-10, and the second crystallizer unit was operated at a temperature of −18° C. The process simulation tool used to perform the simulation was Aspen Plus version 8.8, in which the crystallizer units were customized to model performance based on the SLE model described in the present disclosure.

With a feed mixture in line 211 composed of 25 kg of 3,3'-DMBP, 55 kg of 3,4'-DMBP and 20 kg of 4,4'-DMBP, the simulation predicted the following compositions in the lines listed above:

18.0 kg of pure 4,4'-DMBP recovered in line 213;
25.2 kg of 3,3'-DMBP, 65.6 kg of 3,4'-DMBP and 7.3 kg of 4,4'-DMBP in line 214;
0.2 kg of 3,3'-DMBP, 10.6 kg of 3,4'-DMBP and 5.3 kg of 4,4'-DMBP in line 216;
25 kg of 3,3'-DMBP, 55 kg of 3,4'-DMBP and 2.0 kg of 4,4'-DMBP in line 217;
31.5 kg of pure 3,4'-DMBP recovered in line 219; and
25 kg of 3,3'-DMBP, 23.5 kg of 3,4'-DMBP and 2.0 kg of 4,4'-DMBP in line 221.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including," and whenever a composition, an element or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

The invention claimed is:

1. A process for producing 3,4'- and 4,4'-dimethylbiphenyl, the process comprising:
(a) cooling a feed mixture comprising at least 3,3'-, 3,4'- and 4,4'-dimethylbiphenyl to produce (i) a first crystallization product comprising at least part of the 4,4'-dimethylbiphenyl from the feed mixture, and (ii) a first mother liquor product;

(b) distilling at least part of the first mother liquor product to produce a bottoms stream enriched in 4,4'-dimethylbiphenyl as compared with the first mother liquor product and an overhead stream depleted in 4,4'-dimethylbiphenyl as compared with the first mother liquor product; and (c) cooling at least part of the overhead stream to produce (i) a second crystallization product comprising at least part of the 3,4'-dimethylbiphenyl from the overhead stream, and (ii) a second mother liquor product.

2. The process of claim 1, wherein the cooling step (a) comprises cooling the feed mixture to a first temperature from −30 to 40° C.

3. The process of claim 2, wherein the cooling step (a) comprises cooling the feed mixture to a first temperature from −6 to 40° C.

4. The process of claim 1, wherein the cooling step (c) comprises cooling at least part of the overhead stream to a second temperature of less than −6° C.

5. The process of claim 1, wherein at least part of the bottoms stream is recycled to the cooling step (a).

6. The process of claim 1, wherein the first crystallization product comprises at least 75 wt % 4,4'-dimethylbiphenyl based on the weight of the first crystallization product, and/or wherein the second crystallization product comprises at least 75 wt % 3,4'-dimethylbiphenyl based on the weight of the second crystallization product.

7. The process of claim 1, wherein the distilling step (b) is operated at sub-atmospheric pressure.

8. The process of claim 1, wherein the distilling step (b) is operated at a pressure below 100 mm Hg.

9. The process of claim 1, and further comprising:
(d) isomerizing at least part of the second mother liquor product under conditions effective to increase the concentration of 3,4'- and/or 4,4'-dimethylbiphenyl and produce an isomerization product.

10. The process of claim 9 and further comprising:
(e) supplying at least part of the isomerization product to the cooling step (a).

11. The process of claim 1, and further comprising:
(f) distilling a precursor mixture comprising 3,3'-, 3,4'- and 4,4'-dimethylbiphenyl and at least one 2,X' (where X' is 2', 3' or 4')-dimethylbiphenyl isomer to produce a first fraction comprising the feed mixture of step (a) and a second fraction comprising at least one 2,X'-dimethylbiphenyl isomer.

12. The process of claim 11 and further comprising:
(g) hydrogenating at least part of the second fraction to convert the at least one 2,X'-dimethylbiphenyl isomer to the corresponding (methylcyclohexyl)toluene isomer and produce a hydrogenation effluent;

(h) transalkylating at least part of the hydrogenation effluent from (i) under conditions effective to produce a transalkylation product comprising more 3,Y' and 4,Y' (where Y' is 3 or 4)-(methylcyclohexyl)toluene isomers than the hydrogenation effluent; and (i) dehydrogenating at least part of the transalkylation product to produce a dehydrogenation product comprising more 3,Y' and 4,Y'-dimethylbiphenyl isomers than the second fraction.

13. The process of claim 1, and further comprising:
(j) contacting toluene with hydrogen in the presence of a hydroalkylation catalyst under conditions effective to produce a hydroalkylation reaction product comprising (methylcyclohexyl)toluenes;

(k) dehydrogenating at least part of the hydroalkylation reaction product in the presence of a dehydrogenation catalyst under conditions effective to produce a dehydrogenation reaction product comprising a mixture of dimethylbiphenyl isomers; and (l) employing at least part of the dehydrogenation reaction product as the feed mixture in (a).

14. The process of claim 1, and further comprising:
(m) contacting benzene with hydrogen in the presence of a hydroalkylation catalyst under conditions effective to produce a reaction product comprising cyclohexylbenzenes;

(n) dehydrogenating at least part of the reaction product in the presence of a dehydrogenation catalyst under conditions effective to produce a dehydrogenation reaction product comprising biphenyl;

(o) reacting at least part of the dehydrogenation reaction product with a methylating agent in the presence of an alkylation catalyst under conditions effective to produce a methylation reaction product comprising a mixture of dimethylbiphenyl isomers; and (p) employing at least part of the methylation reaction product as the feed mixture in (a).

15. The process of claim 1, and further comprising:
(q) contacting benzene with oxygen and/or heat, optionally in the presence of an oxidative coupling catalyst, under conditions effective to produce a reaction product comprising biphenyl;

(r) reacting at least part of the biphenyl with a methylating agent in the presence of an alkylation catalyst under conditions effective to produce a methylation reaction product comprising a mixture of dimethylbiphenyl isomers; and (s) employing at least part of the methylation reaction product as the feed mixture in (a).

* * * * *